(12) United States Patent
El Guindi

(10) Patent No.: US 11,477,583 B2
(45) Date of Patent: Oct. 18, 2022

(54) STRESS AND HEARING DEVICE PERFORMANCE

(71) Applicant: Sonova AG

(72) Inventor: Nadim El Guindi, Zurich (CH)

(73) Assignee: Sonova AG, Staefa (CH)

(*) Notice: Subject to any disclaimer, the term of this patent is extended or adjusted under 35 U.S.C. 154(b) by 280 days.

(21) Appl. No.: 16/830,342

(22) Filed: Mar. 26, 2020

(65) Prior Publication Data

US 2021/0306771 A1 Sep. 30, 2021

(51) Int. Cl.
| | | |
|---|---|---|
| *H04R 25/00* | (2006.01) |
| *A61B 5/16* | (2006.01) |
| *A61B 5/00* | (2006.01) |
| *A61B 5/024* | (2006.01) |
| *A61B 5/01* | (2006.01) |
| *A61B 5/053* | (2021.01) |
| *A61B 5/08* | (2006.01) |
| *G10L 25/51* | (2013.01) |
| *A61B 5/369* | (2021.01) |

(52) U.S. Cl.
CPC .............. *H04R 25/505* (2013.01); *A61B 5/01* (2013.01); *A61B 5/02416* (2013.01); *A61B 5/02438* (2013.01); *A61B 5/053* (2013.01); *A61B 5/0816* (2013.01); *A61B 5/165* (2013.01); *A61B 5/369* (2021.01); *A61B 5/4266* (2013.01); *A61B 5/4803* (2013.01); *A61B 5/4836* (2013.01); *A61B 5/6815* (2013.01); *A61B 5/7267* (2013.01); *G10L 25/51* (2013.01); *H04R 25/554* (2013.01); *H04R 25/558* (2013.01); *A61B 2562/0219* (2013.01); *H04R 2225/41* (2013.01)

(58) Field of Classification Search
CPC ....... A61B 5/01; A61B 5/02438; A61B 5/053; A61B 5/4803; H04R 25/505; H04R 25/554; H04R 25/558; H04R 2225/41
See application file for complete search history.

(56) References Cited

U.S. PATENT DOCUMENTS

| | | |
|---|---|---|
| 6,330,339 B1 | 12/2001 | Ishige et al. |
| 6,607,484 B2 | 8/2003 | Suzuki |
| 6,823,312 B2 | 11/2004 | Mittal |
| 7,783,066 B2 | 8/2010 | Naylor |
| 7,970,146 B2 | 6/2011 | Baechler |

(Continued)

FOREIGN PATENT DOCUMENTS

| | | |
|---|---|---|
| EP | 1432282 B1 | 4/2013 |
| EP | 3021599 A1 | 5/2016 |

(Continued)

*Primary Examiner* — Brian Ensey
(74) *Attorney, Agent, or Firm* — ALG Intellectual Property, LLC

(57) ABSTRACT

The disclosed technology generally relates to a hearing device configured to adjust its settings when it detects the hearing device user is experiencing stress related to the hearing device applying a processing scheme. The hearing device can use vital signs of the hearing device user to determine whether a user is stressed. The hearing device can also determine whether the user has become stressed as a result of applied setting or an applied processing scheme of the hearing device based on a change in the vital sign of the hearing device user. The disclosed technology also includes a method for reducing stressing when using a hearing device.

18 Claims, 4 Drawing Sheets

(56) References Cited

U.S. PATENT DOCUMENTS

| | | |
|---|---|---|
| 9,173,043 B2 | 10/2015 | Bulow et al. |
| 9,226,090 B1 | 12/2015 | Norris |
| 9,232,904 B2 | 1/2016 | Morikawa et al. |
| 9,723,415 B2 | 8/2017 | Gran et al. |
| 9,987,489 B2 | 6/2018 | Goodall |
| 10,015,601 B2 | 7/2018 | Frederiksen et al. |
| 10,078,859 B2 | 9/2018 | Sable |
| 10,117,032 B2 | 10/2018 | Gordon |
| 10,129,664 B2 | 11/2018 | Starkey |
| 2007/0071262 A1 | 3/2007 | Rass |
| 2010/0019686 A1 | 1/2010 | Gutierrez |
| 2010/0196861 A1 | 8/2010 | Lunnter |
| 2010/0278365 A1* | 11/2010 | Biundo Lotito ..... H04R 25/405 381/315 |
| 2011/0150253 A1 | 6/2011 | Corona-Strauss et al. |
| 2012/0183164 A1 | 7/2012 | Foo et al. |
| 2015/0271607 A1 | 9/2015 | Sabin |
| 2015/0289063 A1 | 10/2015 | Ma |
| 2016/0080876 A1 | 3/2016 | Lunner |
| 2016/0100796 A1 | 4/2016 | Lineaweaver |
| 2017/0215011 A1* | 7/2017 | Goldstein ............ H04R 25/305 |
| 2017/0230762 A1 | 8/2017 | Simonides et al. |
| 2020/0268260 A1* | 8/2020 | Tran ................. A61B 1/000096 |

FOREIGN PATENT DOCUMENTS

| | | |
|---|---|---|
| EP | 3154278 A1 | 4/2017 |
| WO | 2001054456 A1 | 7/2001 |
| WO | 2008009142 A1 | 1/2008 |
| WO | 2012072141 A1 | 6/2012 |
| WO | 2017211426 A1 | 12/2017 |

\* cited by examiner

STRESS AND HEARING DEVICE PERFORMANCE

TECHNICAL FIELD

The disclosed technology generally relates to a hearing device configured to adjust its settings when it detects the hearing device user is experiencing stress related to the hearing device applying a processing scheme.

BACKGROUND

Satisfactory performance of a hearing device can be related to several factors. The size and shape of the hearing device are examples of such factors. If the hearing device is physically too small or not the right shape, the hearing device user may find the hearing device does not physically fit well or causes some discomfort when in use. If the hearing device user does not find the hearing device to physically fit well, the hearing device user is unlikely to use the hearing device or use it less frequently, which can prolong the adoption of using a hearing device.

While physical parameters of the hearing device can lead to user dissatisfaction and even rejection of the hearing device, the fitting of settings of the hearing device can also influence emotional and mental factors that may also lead to the rejection of a hearing device. Fitting settings of the hearing device generally refer to the programming of the hearing device used to adjust audio signals provided to a hearing device user (also referred to as "fit" for a hearing device). The fitting of a hearing device can be based on a meeting with a hearing care professional (HCP), and the HCP performing a hearing test. Based on the hearing test, the HCP can use fitting software to program a hearing device to be fit for a user's hearing loss. If a fitting of a hearing device is not correct for a hearing device user (e.g., too difficult to hear, too soft, too loud), the hearing device user may experience emotional or mental stress that causes dissatisfaction with the hearing device.

Further, it is even possible that a hearing device is in fact fit properly for the hearing device user, but a sound environment is causing emotional stress for the hearing device user because the user has not adopted to the fit or prefers another setting in a sound environment. In such cases, it is difficult for a hearing device user to become fully comfortable with the hearing device, which may prolong or end the adoption process. For example, in the US, more than half of hearing aid first time users return hearing aids after a trial period even after meeting with an HCP for a proper fitting.

Accordingly, there exists a need to provide technology that enables the hearing device user to be satisfied and provide additional benefits.

SUMMARY

This summary is provided to introduce a selection of concepts in a simplified form that are further described below in the Detailed Description. This summary is not intended to identify key features of the claimed subject matter.

The disclosed technology includes a hearing device comprising a microphone, a sensor (e.g., accelerometer, temperature sensor, heart monitor, EEG, PPG), a processor, and a memory electronically coupled to the processor. The memory can store instructions that when executed by the processor cause the hearing device to perform operations. The operations can comprise: determine a classification of sound associated with the audio signal; determine that a vital sign associated with stress of the hearing device user has exceeded a stress threshold; and based on the determined classification of the sound and in response to determining the stress threshold has been exceeded, adjust a setting of the hearing device or provide an option to implement an alternative setting.

The disclosed technology also includes a method for operating a hearing device. The method comprises: receiving a vital sign for a hearing device user from a sensor of a hearing device worn by the hearing device user; determining a classification of sound received by the microphone of the hearing device; determining a signal processing scheme to apply to the received sound based on the classification of the received sound; providing an output to the hearing device user based on the signal processing scheme; determining whether the applied signal processing scheme causes the hearing device user stress based on detecting a change in the vital sign of the hearing device user in response to providing the sound; and in response to determining the hearing device user is stressed, adjusting a setting of the hearing device or providing an option to implement an alternative setting. The method can be stored on a non-transitory computer-readable medium.

Figure 1:
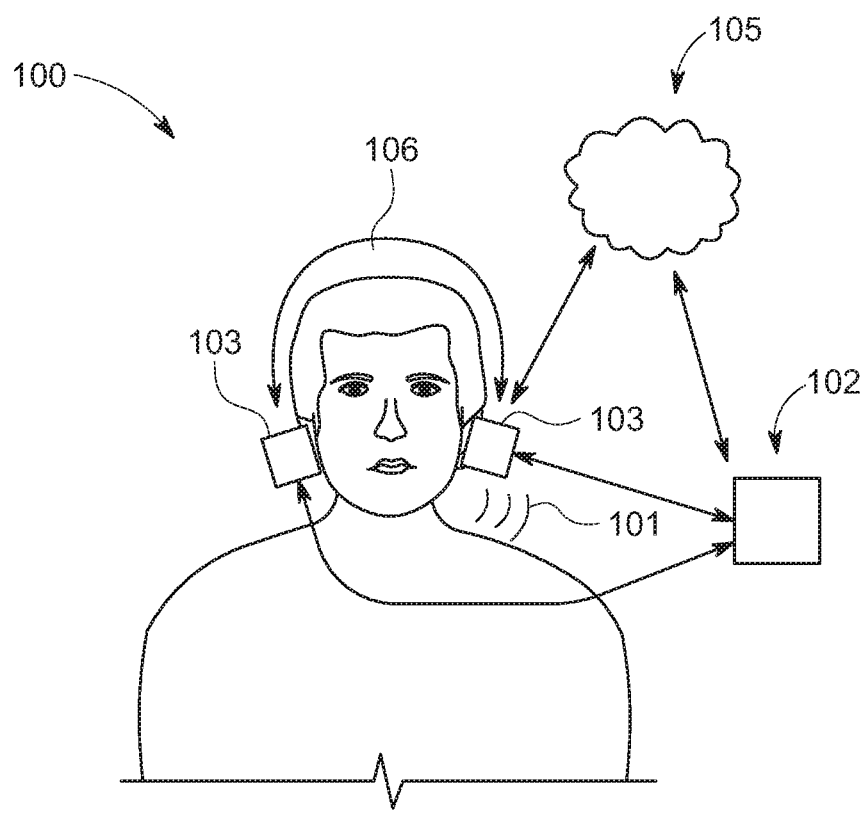
FIG. 1 illustrates a communication environment with a hearing device user wearing hearing devices in accordance with some implementations of the disclosed technology.

The drawings are not to scale. Some components or operations may be separated into different blocks or combined into a single block for the purposes of discussion of some of the disclosed technology. Moreover, while the technology is amenable to various modifications and alternative forms, specific implementations have been shown by way of example in the drawings and are described in detail below. The intention, however, is not to limit the technology to the selected implementations described. On the contrary, the technology is intended to cover all modifications, equivalents, and alternatives falling within the scope of the technology as defined by the appended claims.

DETAILED DESCRIPTION

If a hearing device user is experiencing stress while using a hearing device, the stress can cause the hearing device user to become frustrated or uncomfortable while using the hearing device, which discourages the hearing device user from using the hearing device. For example, a hearing device user can become stressed if a hearing device implements a setting that is incorrect or uncomfortable (e.g., too soft, or too loud) for a particular sound environment. When a setting is incorrect or uncomfortable, it can cause the user to apply more effort in listening and/or understanding to overcome stress, and if the user cannot overcome this stress the hearing device user may take off the hearing device and return it or not use if for a long period of time. Also, applying more effort can be tiring and/or exhausting and lead to more stress, which can result in compounding stress until a user reaches a "give up point" where he or she needs to take a break or stop what he or she is doing. If a hearing device user continues to experience stress when using the hearing device, it may cause the hearing device user to not adapt to the device over time and ultimately not allow the hearing device user to adapt to the full capability of the device.

Furthermore, in some cases, a hearing device is fit properly for a hearing device user, but the hearing device user becomes stressed and then it becomes difficult for him or her to feel comfortable using the hearing device. In such cases, it is valuable if the hearing device changes its settings temporary to reduce the user's stress and returns to the pre-stressed settings after the user can relax. This can allow the hearing device to adopt and acclimate to the hearing device. Such adjustments can help a hearing device user adopt to settings over time and reduce the rate at which hearing device users return or give up on hearing devices.

To reduce or avoid stress associated with wearing a hearing device or in the process of fitting a hearing device, the hearing device can measure a vital sign of a hearing device user that is associated with stress. When the hearing device determines that the stress of the user has exceeded a threshold based on the vital sign it can adjust a setting of the hearing device or provide an alternative setting option to reduce the stress. For example, if a hearing device is using its beam former to focus on sound arriving from the front of a hearing device user and then the hearing device determines that the heart rate of the hearing device user increased beyond a stress threshold as a result of the beam former setting, the hearing device can either automatically reduce the beam former setting to widen the beam, turn off the beam former, or provide the hearing device user with an option to manually adjust the beam former (e.g., to turn beam forming off). The automatic adjustment or the option can result in a more relaxed or comfortable setting designed to reduce stress of the hearing device user.

As another example, when a hearing device user is stress, the hearing device can determine that a user is having trouble understanding speech because the hearing device user is frequently stating he or she cannot hear or understand (e.g., "can you repeat that?" or "I don't understand what you are saying"), and the hearing device can switch the hearing device from a mode of high speech intelligibility to a comfort mode to reduce the stress associated with not hearing or understanding. This change in mode of the hearing device can cause the hearing device user to relax and experience a reduction in stress. When the user feels less stressed, he or she can re-activate the original settings of the hearing device such that in can transition to higher intelligibility. Alternatively, the hearing device can automatically determine that a vital sign indicates the user is no longer stressed, and return the device to its original settings.

The disclosed technology can have a technical benefit and/or address a technical problem for reducing stress for hearing device users. When the hearing device determines that a hearing device user is stressed, the hearing device can change the settings of the hearing device or provide an alternative option. This allows the hearing device user to experience less stress and this can improve the hearing device user's experience with the device. Because the hearing device user becomes less stressed when using the device, the hearing device user is more likely to use the device and acclimatize to using a hearing device (e.g., adopt the fitting of the hearing device). Specifically, because the hearing device can switch between settings to reduce stress, over time, the hearing device user can build up tolerance to different settings and grow to endure for stressful situations.

Additionally, in some implementations, the hearing device can record what sound environments cause a user stress and whether an applied signal processing improved, worsened, or maintained the level of stress for the hearing device user. A signal processing scheme or signal processing setting generally refers to the modification of an audio signal based on digital signal processing operations (e.g., amplification, filtering, gain, beam forming, etc.). This recorded information can be logged on a server and used in a machine learning algorithm to provide recommended settings of a hearing device for stressful situations.

FIG. 1 illustrates a communication environment 100. The communication environment 100 includes wireless communication devices 102 (singular "wireless communication device 102" and multiple "wireless communication devices 102") and hearing devices 103 (singular "hearing device 103" or multiple "hearing devices 103"). As shown by voice 101, the hearing device user can speak and generate sound waves.

As shown by double-headed bold arrows in FIG. 1, the wireless communication devices 102 and the hearing devices 103 can communicate wirelessly, e.g., each wireless communication device 102 can communicate with each hearing device 103 and each hearing device 103 can communicate with the other hearing device. Wireless communication can include using a protocol such as Bluetooth BR/EDR™, Bluetooth Low Energy™, a proprietary communication (e.g., binaural communication protocol between hearing aids based on NFMI or bimodal communication protocol between hearing devices), ZigBee™, Wi-Fi™, or an Industry of Electrical and Electronic Engineers (IEEE) wireless communication standard.

The wireless communication devices 102 are computing devices that are configured to wirelessly communicate. Wireless communication includes wirelessly transmitting information, wirelessly receiving information, or both. The wireless communication devices 102 shown in FIG. 1 can include mobile computing devices (e.g., mobile phone), computers (e.g., desktop or laptop), televisions (TVs) or components in communication with television (e.g., TV streamer), a car audio system or circuitry within the car, tablet, remote control; an accessory electronic device, a wireless speaker, or watch.

A hearing device user can wear the hearing devices 103 and the hearing device 103 provides audio to a hearing device user. For example, a hearing device user can wear single hearing device 103 or two hearing devices 103, where one hearing device 103 is on each ear. Some example hearing devices include hearing aids, headphones, earphones, assistive listening devices, or any combination thereof; and hearing devices include both prescription devices and non-prescription devices configured to be worn on or near a human head.

As an example of a hearing device, a hearing aid is a device that provides amplification, attenuation, or frequency modification of audio signals to compensate for hearing loss or difficulty; some example hearing aids include a Behind-the-Ear (BTE), Receiver-in-the-Canal (RIC), In-the-Ear (ITE), Completely-in-the-Canal (CIC), Invisible-in-the-Canal (IIC) hearing aids or a cochlear implant (where a cochlear implant includes a device part and an implant part).

The hearing devices 103 are configured to binaurally or bimodally communicate. The binaural communication can include a hearing device 103 transmitting information to or receiving information from another hearing device 103. Information can include volume control, signal processing information (e.g., noise reduction, wind canceling, directionality such as beam forming information), or compression information to modify sound fidelity or resolution. Binaural communication can be bidirectional (e.g., between hearing devices) or unidirectional (e.g., one hearing device receiving or streaming information from another hearing device). Bimodal communication is like binaural communication, but bimodal communication includes two devices of a different type, e.g. a cochlear device communicating with a hearing aid.

The network 105 is a communication network. The network 105 enables the hearing devices 103 or the wireless communication devices 102 to communicate with a network or other devices. The network 105 can be a Wi-Fi™ network, a wired network, or a network implementing any of the Institute of Electrical and Electronic Engineers (IEEE) 802.11 standards. The network 105 can be a single network, multiple networks, or multiple heterogeneous networks, such as one or more border networks, voice networks, broadband networks, service provider networks, Internet Service Provider (ISP) networks, and/or Public Switched Telephone Networks (PSTNs), interconnected via gateways operable to facilitate communications between and among the various networks. In some implementations, the network 105 can include communication networks such as a Global System for Mobile (GSM) mobile communications network, a code/time division multiple access (CDMA/TDMA) mobile communications network, a 3rd, 4th or 5th generation (3G/4G/5G) mobile communications network (e.g., General Packet Radio Service (GPRS)) or other communications network such as a Wireless Local Area Network (WLAN).

The network 105 can include or be configured to communication with computing devices and/or servers (not shown in FIG. 1). The servers can store information logged by the hearing devices 103 or the wireless communication devices 102. The servers can also perform machine learning algorithms on data received from the hearing devices 103. For example, the servers can receive data related to received sound, classification of the received sound, vital sign(s) of the hearing device user, and applied signal processing schemes for the hearing devices 103. Using the machine learning algorithms, the servers can determine recommended hearing device settings for a hearing device user in a stressful situation.

Figure 2:
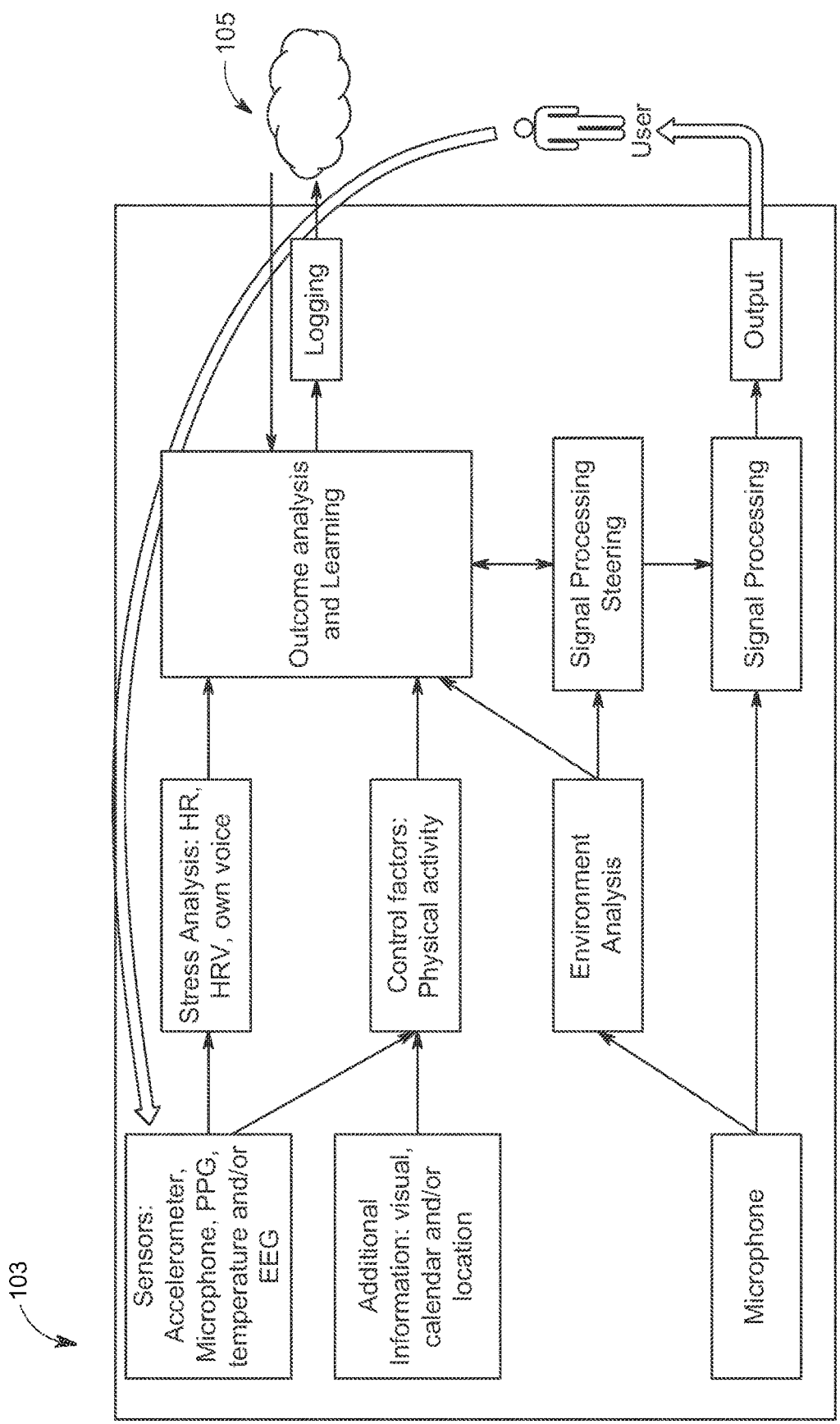
FIG. 2 illustrates a thematic block flow diagram for a hearing device from FIG. 1 implementing the disclosed technology in accordance with some implementations of the disclosed technology.

FIG. 2 illustrates a thematic block flow diagram for a hearing device from FIG. 1 implementing the disclosed technology. FIG. 2 illustrates the hearing device 103 that is worn by a user (shown on the right side of FIG. 2), and the hearing device can exchange information with the network 105 as described with respect to FIG. 1 (right side of FIG. 2). The hearing device 103 can detect information related to a user's vital signs to determine whether a user is stressed, it can use control factors to control for stress not related to hearing device processing schemes (e.g., physical activity such as running associated with a high heart rate), and it can learn from the outcomes of different sound environments and signal processing schemes.

The hearing device 103 can receive vital sign information from the sensors. Vital sign information generally refers measurements of a human state such as pulse rate, temperature, respiration rate, blood pressure, concentration of elements in blood (e.g., oxygen). The information can be received from an accelerometer, microphone, photoplethysmogram (PPG) sensor, temperature sensor, and/or Electroencephalography (EEG) sensor.

The vital sign information from the sensors can be used to analyze stress of the hearing device user. The stress analysis can be based on heart rate (HR), heart rate variability (HRV), changes in acceleration, or own voice of the hearing device user. For example, if a hearing device user has a high heart rate, it can be determined that the hearing device user is stressed. Also, if the hearing device user experiences an acute change in a heart rate or variability in heart rate, it can be determined that the hearing device user is stressed. Thresholds (i.e., specific values or ranges of values) can be used to establish when a user is stressed. For example, a pulse rate of greater than 80 can indicate a user is stressed. The correlation between heart rate, heart rate variability, and stress is further described in *Effects of Stress on Heart Rate Complexity-A comparison between short-term and chronic stress*, which published on Mar. 1, 2009 in the Biological Psychology Volume 80, Issue 3, pages 325-332, and is incorporated by reference herein for its entirety. Citation: Schubert C, Lambertz M, Nelesen R A, Bardwell W, Choi J B, Dimsdale J E. Effects of stress on heart rate complexity—a comparison between short-term and chronic stress. Biol Psychol. 2009; 80(3):325-332. doi:10.1016/j.biopsycho.2008.11.005

Also, the hearing device 103 can detect a user's own voice and parameters of the user's own voice to analyze whether a user is stressed. The correlation between a user's own voice and stress is further described in *Voice Stress Analysis: A New Framework for Voice and Effort in Human Performance*, Van Puyvelde M, Neyt X, McGlone F, Pattyn N. Front Psychol. 2018; 9:1994. Published 2018 Nov. 20. doi:10.3389/fpsyg.2018.01994, which is incorporated by reference herein for its entirety.

In some implementations, the hearing device 103 can also incorporate additional information to use as control factors for determining whether a hearing device user is stressed. For example, the hearing device 103 can wirelessly connect to a mobile phone for the hearing device user to determine visual, calendar, and/or location information. Based on this additional information, the hearing device 103 can determine that hearing device user is stressed for reasons other than an applied processing scheme or setting of the hearing device. For example, a user's calendar may indicate that a hearing device user is in a physical fitness class and experiencing physical stress from working out. Based on this calendar information, the hearing device can determine not to adjust settings of the hearing device based on stressed.

Also, the hearing device may determine based on a user's location that the hearing device user is more likely to be stress from the environment. For example, the location can indicate that the hearing device user is at the hospital or work, locations where the hearing device user may experience elevated levels of stress. The hearing device can incorporate this additional information to evaluate whether a user is stressed based on location. More information regarding the correlation between location, machine learning, and stress of a person can be found in Ahuja, Ravinder & Banga, Alisha. (2019), Mental *Stress Detection in University Students using Machine Learning Algorithms*. Procedia Computer Science. 152. 349-353. 10.1016/j.procs.2019.05.007, which is incorporated by reference herein for its entirety.

As shown on right side of FIG. 2, information related to vital signs or a hearing device user and whether a user is stress can be provided for learning analysis. For example, the hearing device can determine how a user's stress level changed based on an applied signal processing steering (e.g., parameters of the beam former). The learning can be logged and provided to the computer network 105 for further analysis (e.g., machine learning).

The information related to vital signs from the sensors, the additional information related to the user, the control factors, and sound received at the microphone (e.g., used to determine sound environment) can be used to determine how to adjust or apply signal processing schemes to the hearing device as shown at the bottom of FIG. 2. The output of the hearing device can be an audio signal or sound (e.g., modified by the processor of the hearing device).

Figure 3:
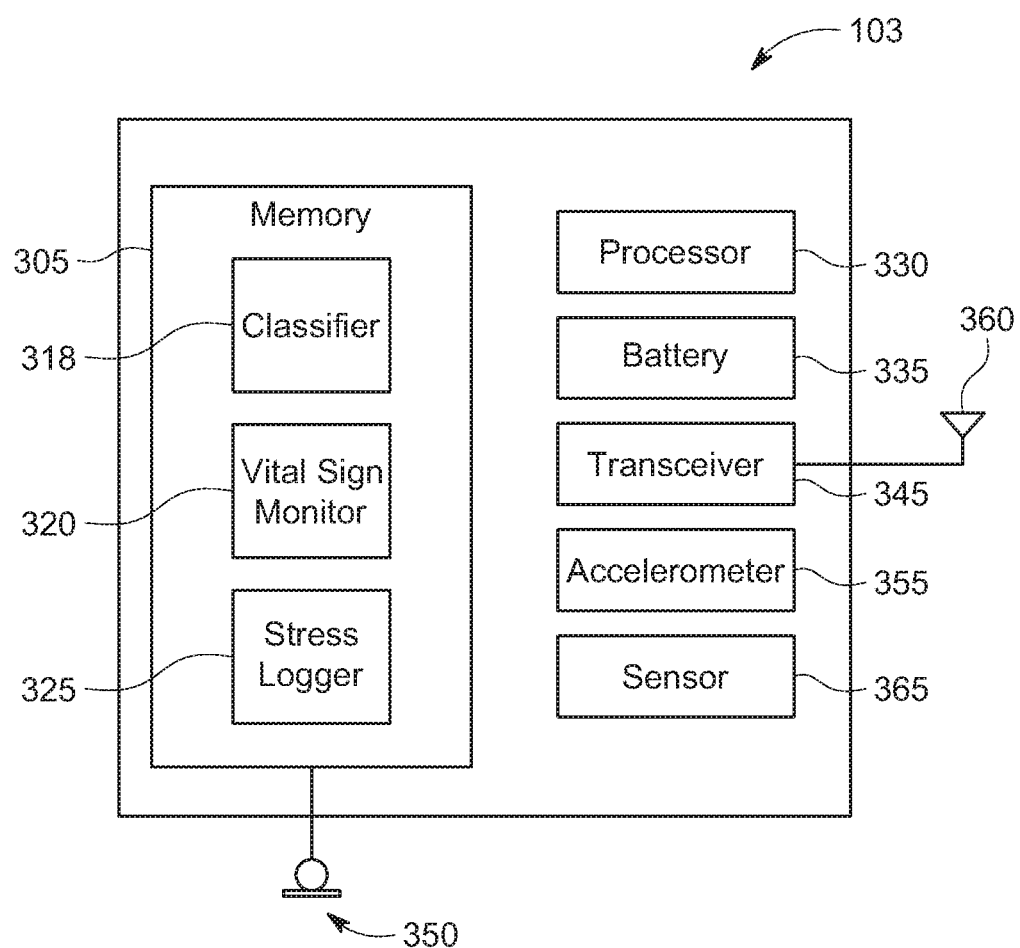
FIG. 3 illustrates a hearing device from FIG. 1 in more detail in accordance with some implementations of the disclosed technology.

FIG. 3 is a block diagram illustrating the hearing device 103 from FIG. 1 in more detail. FIG. 3 illustrates the hearing device 103 with a memory 305, software stored in the memory 305, the software includes a classifier 318, vital sign monitor 320, and stress logger 325. The hearing device 103 also has a processor 330, a battery 335, a transceiver 345 coupled to an antenna 360, an accelerometer 355 (also referred to as a "first sensor"), a sensor 365 (also referred to as "a second sensor"), and a microphone 350. Each of these components is described below in more detail.

The memory 305 stores instructions for executing software comprised of one or more modules and data utilized by the modules. The modules perform certain methods or functions for the hearing device 103 and can include components, subcomponents, or other logical entities that assist with or enable the performance of these methods or functions. Although a single memory 305 is shown in FIG. 3, the hearing device 103 can have multiple memories 305 that are partitioned or separated, where each memory can store different information.

The classifier 318 can sample the current acoustic environment and generate probabilities for each of the listening destinations available in the automatic programming of the hearing device 103. The classifier 318 can switch to the listening program for which the highest probability is generated. The classifier 318 can determine the classification to be speech in quiet, small group, large group, conversation in noise, noise, music, or quiet. For example, the classifier 318 can switch from applying a signal processing scheme for speech-in-noise to a signal processing scheme for quite based on determining that there is a little or no sound received at the microphone 350.

The classifier 318 can switch again when the acoustic environment changes enough such that another listening environment generates a higher probability. The classifier 318 can use cluster analysis of envelope modulation, spectral features of audio signals, hidden Markov Models, Gaussian mixture models, support vector machines, neural networks, and/or Bayesian classifiers. The classifier 318 can communicate with the processor 330 and the processor 330 can use digital signal processing algorithms to provide the classifier 318 with relevant audio signal information. In some implementations, the classifier 318 is part of a digital signal processor (DSP), which is a part of the processor 330. The classifier 318 can adjust a beam former of a hearing device.

The vital sign monitor 320 can receive and analyze vital sign signals from the sensor 365, the microphone 350, and/or the accelerometer 355. The vital sign monitor 320 can receive signals associated with heart rate, heart rate variability, pulse, voice, motion or acceleration, temperature, or other vital sign signals. The vital sign monitor 320 can determine whether the vital signs of a hearing device user have exceeded a threshold that indicates the hearing device user is stressed. The threshold can be based on standard medical thresholds (as discussed above in FIG. 2) or based on learned thresholds for a population of hearing device users or the specific hearing device user (e.g., calibrated to the hearing device user). For example, if a hearing device user's pulse exceeds 80 bpm, the vital sign monitor 320 can determine that the hearing device user is stressed. The vital sign monitor 320 can also continuously monitor vital signs or only monitor when the hearing device user has requested it.

The stress logger 325 is configured to log data related to the stress of the user such as vital signs, applied signal processing scheme, and/or sound received at the hearing device microphone 350 when a user is experiencing stress. The stress logger 325 can store this information and transmit it to a wireless device 102. The wireless device 102 can use it perform machine learning algorithms and provide the stress logger with analysis.

The processor 330 can include special-purpose hardware such as application specific integrated circuits (ASICs), programmable logic devices (PLDs), field-programmable gate arrays (FPGAs), programmable circuitry (e.g., one or more microprocessors microcontrollers), Digital Signal Processor (DSP), Neural network engines, appropriately programmed with software and/or computer code, or a combination of special purpose hardware and programmable circuitry.

Also, although the processor 330 is shown as a separate unit in FIG. 2, the processor 330 can be on a single chip with the transceiver 345, and the memory 305. The processor 330 can also include a DSP configured to modify audio signals based on hearing loss or hearing programs stored in the memory 305. In some implementations, the hearing device 103 can have multiple processors, where the multiple processors can be physically coupled to the hearing device 103 and configured to communicate with each other.

The battery 335 can be a rechargeable battery (e.g., lithium ion battery) or a non-rechargeable battery (e.g., Zinc-Air) and the battery 335 can provide electrical power to the hearing device 103 or its components. In general, the battery 335 has significantly less available capacity than a battery in a larger computing device (e.g., a factor 100 less than a mobile phone device and a factor 1000 less than a laptop).

The accelerometer 355 can be used to measure changes in acceleration of the hearing device. These changes can be associated with the user exercising, moving their head, walking, running, speaking, or shaking, which can also be used to determine whether a user is stressed. The accelerometer 355 can be positioned inside the hearing device. The accelerometer 355 can be a capacitive accelerometer, a piezoelectric accelerometer, or another type of accelerometer. In some implementations, the accelerometer can measure acceleration along only a single axis. In other implementations, the accelerometer can sense acceleration along two axes or three axes. For example, the accelerometer can create a 3D vector of acceleration in the form of orthogonal components. The accelerometer 355 can output a signal that is received by the processor 330 (e.g., including raw data). The acceleration can be output in meters/second$^2$ or g's (1 g=9.81 meters/second$^2$). In some implementations, the accelerometer can detect acceleration changes from −2 g's to +2 g's or −16 g's to +16 g's sampled at a frequency of greater than 100 Hz, e.g., 200 Hz. For physical activity detection and head movement, 25 Hz or 50 Hz is sufficient. For fall detection or tap detection, 100 Hz or 200 Hz is sufficient.

The accelerometer 355 can also be in a housing of the hearing device, where the housing is located behind a user's ear. Alternatively, the accelerometer 355 can be in a housing for a hearing device, wherein the housing is inside a user's ear canal or at least partially inside a user's ear. The accelerometer 355 can be an ultra-low power device, wherein the power consumption is less than 10 micro Amps (μA). The accelerometer 355 can be a micro-electro-mechanical system (MEMS) or nanoelectromechanical system (NEMS).

In some implementations, instead of the accelerometer 355, the component for detecting a change in acceleration can be gyro or magnetometer. The component for detecting a change in acceleration can measure inertial on different axes.

The sensor 365 is configured to provide a vital sign signal that can be used to determine whether a hearing device user is stressed. The sensor 365 can also be referred to as the second sensor (e.g., because the accelerometer 355 is the first sensor). The sensor 365 can be a EEG sensor, PPG sensor, photodiode sensor, temperature sensor, optical sensor, or capacitive sensor. The temperature sensor can measure a change in temperature an ear or part of an ear where the hearing device is located. The optical sensor can be used to measure heart rate. The sensor 365 can provide a vital sign signal to the processor 330, where the vital sign signal generally includes information about a monitored vital sign of the hearing device user.

The microphone 350 is configured to capture sound and provide an audio signal of the captured sound to the processor 330. The microphone 350 can also convert sound into audio signals. The processor 330 can modify the sound (e.g., in a DSP) and provide the processed audio derived from the modified sound to a user of the hearing device 103. Although a single microphone 350 is shown in FIG. 2, the hearing device 103 can have more than one microphone. For example, the hearing device 103 can have an inner microphone, which is positioned near or in an ear canal, and an outer microphone, which is positioned on the outside of an ear. As another example, the hearing device 103 can have two microphones, and the hearing device 103 can use both microphones to perform beam forming operations. In such an example, the processor 330 would include a DSP configured to perform beam forming operations.

The antenna 360 can be configured for operation in unlicensed bands such as Industrial, Scientific, and Medical Band (ISM) using a frequency of 2.4 GHz. The antenna 360 can also be configured to operation in other frequency bands such as 5.8 GHz, 3.8 MHz, 10.6 MHz, or other unlicensed bands.

Also, the hearing device 103 can include an own voice detection unit configured to detect a voice of the hearing device user and separate such voice signals from other audio signals (not shown). To implement detecting own voice, the hearing device can include a second microphone configured to convert sound into audio signals, wherein the second microphone is configured to receive sound from an interior of an ear canal and positioned within the ear canal, wherein a first microphone is configured to receive sound from an exterior of the ear canal. The hearing device can also detect own voice of a hearing device user based on other implementations (e.g., a digital signal processing algorithm that detects a user's own voice). The own voice detection unit can be used to determine what the user said and other parameters of the user's speech.

Figure 4:
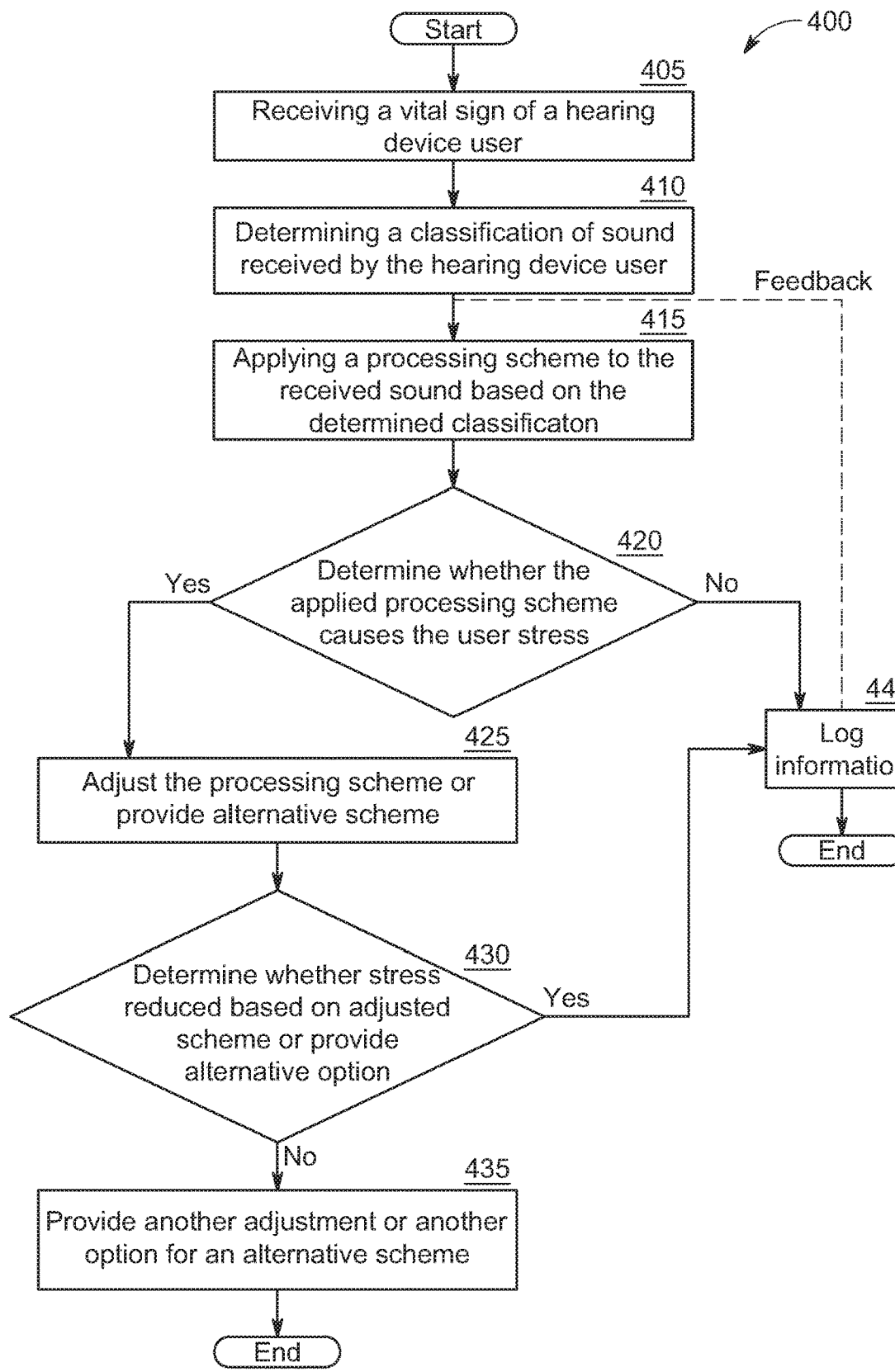
FIG. 4 is a block flow diagram illustrating a process to reduce stress when using a hearing device in accordance with some implementations of the disclosed technology.

FIG. 4 illustrates a block flow diagram for a process 400 for reducing stress for a hearing device user. The hearing device 103 and/or another computing device can perform part or all of the process 400. The process 400 can begin with receiving a vital sign operation 405 and continue to determine classification operation 410.

At the receiving a vital sign operation 405, a hearing device can receive a vital sign of a hearing device user. The vital sign can be heart rate, heart rate variability, temperature, voice of the hearing device user, breathing pattern, movement or acceleration, or other medical sign associated with the hearing device user. The vital sign can be received from a sensor or microphone on the hearing device as disclosed in FIGS. 2 and 3. In some implementations, the hearing device can receive multiple vital signs (e.g., temperature and heart rate or heart rate and voice).

At classification operation 410, the hearing device can classify the sound received at its microphone. The hearing device can use its classifier to determine the class of the received sound at a hearing device is speech in quiet, speech in noise, small group, large group, conversation in noise, noise, music, or quiet. The classification operation 410 can be performed automatically by a processor. Additionally, as explained in FIG. 3, the classifier can determine a class of sound based on the probability determined for a class, but the classifier can also determine the "next most likely" classifier for sound received at a hearing device based on the second highest probability. The different classifications of sound can be stored in the memory can used for logging data and/or providing alternative settings for the hearing device.

At apply processing scheme operation 415, the hearing device applies a processing scheme operation when providing audio signals to hearing device user. The applied processing scheme can be based on the classification sound from operation 410. For example, if the classifier determines that hearing device is listening to music, it can apply a digital processing scheme that optimizes the output of the hearing device for listening to music. The digital processing scheme (also referred to as "processing scheme") can depend on the fit of the hearing device and the preferences of the hearing device user. As another example, the hearing device can apply a beam forming operation to focus on a conversation in front of the user based on determining that classified sound is classified as small group conversation. The applied digital processing scheme can process audio signals such that sound related to the conversation is amplified (e.g., the SNR for signals from the front of the hearing device is increased).

At determine stress operation 420, the hearing device determines whether a hearing device user is stressed by the applied processing scheme. Based on the received vital sign from operation 405, the hearing device can determine whether a stress threshold of a vital signal has been exceeded. For example, the hearing device can determine whether the user's pulse rate or heart variability has increased above a threshold after the processing scheme was applied. The hearing device can also determine that a hearing device user is stressed based on characteristics of the user's voice as described in FIG. 2 or based on the vocabulary of the user (e.g., "I can't hear" or "I am having trouble understanding" or "I feel stressed"). If the user does not experience stress based on the applied digital processing scheme, the processor 400 can proceed to operation 440 to log the settings of the hearing device and classification of sound. The hearing device can then communicate this logged information to another computing device or network, where this data can be used for machine learning for determine what settings to apply to a hearing device to reduce stress of the hearing device user.

If the hearing device determines that stress was caused by the applied processing scheme, the hearing device adjusts the processing scheme or provides an alternative scheme in operation 425. The hearing device can automatically adjust the processing scheme by changing the classification of the sound to the second highest probability or it can simply switch from an advanced digital processing scheme to a comfort scheme. For example, if the hearing device determines that beam forming operation causes a hearing device user to focus on sound from conversation in front of the hearing device user, but the vital signs of the hearing device user indicate that the user is stressed out by this focus, the hearing device can turn off the beam former or even widen the angle of the beam to reduce the listening effort a hearing device user needs to apply. The automatic change in the processing scheme can cause the output of the hearing device to change, and this can result in the hearing device user being less stressed by the output.

Alternatively, instead of automatically changing the processing scheme, the hearing device can provide the hearing device user with an option to change. For example, the hearing device can send a notification to the hearing device user's phone and ask the user if he or she prefers a different setting (e.g., softer, louder, less focused, or different beam width). The hearing device can also provide the alternative option as an audio signal directly in the ear of the hearing device user (e.g., "you may be experiencing stress based on the applied settings, we recommend tapping the hearing device or pressing its button to change the current setting to a reduced setting that will likely cause less stress").

In determining whether adjustment was effective operation 430, the hearing device determines whether the adjusted setting (e.g., new processing scheme or setting) reduced the stress of the hearing device user or the provided alternative option was used by hearing device user and whether it reduced his or her stress. If the new setting reduced the stress of the hearing device user, this information can be logged in operation 440 and the hearing device can continue operating without a further change. If the hearing device determines that hearing device user is still stressed or the alternative setting was selected and not effective at reducing stress, it can provide even another change or another option to change or it can simply operate in a basic mode. The basic mode would provide a minimum amount of sound modification so that the hearing device user can hear, but without stress. This information can also be logged as a negative hearing device user experience.

The process 400 can be repeated entirely, repeated partially (e.g., repeat only operation 420), or stopped after operation 435 or 440.

The phrases "in some implementations," "according to some implementations," "in the implementations shown," "in other implementations," and generally mean a feature, structure, or characteristic following the phrase is included in at least one implementation of the disclosure, and may be included in more than one implementation. In addition, such phrases do not necessarily refer to the same implementations or different implementations.

The techniques introduced here can be embodied as special-purpose hardware (e.g., circuitry of a hearing device), as programmable circuitry appropriately programmed with software or firmware, or as a combination of special-purpose and programmable circuitry. Hence, implementations may include a machine-readable medium having stored thereon instructions which may be used to program a computer (or other electronic devices) to perform a process. The machine-readable medium may include, but is not limited to, read-only memory (ROM), random access memories (RAMs), erasable programmable read-only memories (EPROMs), electrically erasable programmable read-only memories (EEPROMs), magnetic or optical cards, flash memory, or other type of media/machine-readable medium suitable for storing electronic instructions. In some implementations, the machine-readable medium is non-transitory computer readable medium, where in non-transitory excludes a propagating signal.

The above detailed description of examples of the disclosure is not intended to be exhaustive or to limit the disclosure to the precise form disclosed above. While specific examples for the disclosure are described above for illustrative purposes, various equivalent modifications are possible within the scope of the disclosure, as those skilled in the relevant art will recognize. For example, while processes or blocks are presented in an order, alternative implementations may perform routines having steps, or employ systems having blocks, in a different order, and some processes or blocks may be deleted, moved, added, subdivided, combined, or modified to provide alternative or subcombinations. Each of these processes or blocks may be implemented in a variety of different ways. Also, while processes or blocks are at times shown as being performed in series, these processes or blocks may instead be performed or implemented in parallel, or may be performed at different times. Further any specific numbers noted herein are only examples: alternative implementations may employ differing values or ranges.

As used herein, the word "or" refers to any possible permutation of a set of items. For example, the phrase "A, B, or C" refers to at least one of A, B, C, or any combination thereof, such as any of: A; B; C; A and B; A and C; B and C; A, B, and C; or multiple of any item such as A and A; B, B, and C; A, A, B, C, and C; etc. As another example, "A or B" can be only A, only B, or A and B.

I claim:

1. A hearing device comprising:
a microphone configured to receive sound and convert the sound into an audio signal;
a sensor configured to detect a vital sign associated with stress of a hearing device user and provide a vital sign signal associated with the detected vital sign;
a processor configured to receive the audio signal and the vital sign signal; and
a memory, electronically coupled to the processor, the memory storing instructions that when executed by the processor direct the hearing device to perform operations, the operations comprising:
determine a classification of sound associated with the audio signal;
determine that the vital sign associated with stress of the hearing device user has exceeded a stress threshold;
based on the determined classification of the sound and in response to determining the stress threshold has been exceeded, adjust a setting of the hearing device or provide an option to implement an alternative setting; and
log that the hearing device user is having a negative hearing experience associated with the setting or the alternative setting, wherein the logging includes storing the determined classification of the sound received at the hearing device.

2. The hearing device of claim 1, wherein the sensor comprises: at least one of an accelerometer, a heart rate monitor, a temperature sensor, a photoplethysmogram (PPG)

sensor, a temperature sensor, an Electroencephalography (EEG) sensor, or a skin conductance sensor.

3. The hearing device of claim 1, wherein the operations further comprise:
   receive a user input to implement the alternative setting; and
   in response to the received user input, execute an operation to implement the alternative setting.

4. The hearing device of claim 1, wherein the processor comprises a classifier configured to classify the audio signal, and wherein the adjusting the setting of the hearing device or the providing the option to implement the alternative setting is based on a classification of the audio signal.

5. The hearing device of claim 1, wherein the vital sign is associated with temperature, pulse, a heart measurable parameter, sweat, a breathing pattern, a voice of the hearing device user, or skin conductance.

6. The hearing device of claim 1, wherein the sensor is an accelerometer configured to measure changes in acceleration of the hearing device, and wherein the changes are associated with a breathing pattern.

7. The hearing device of claim 1, wherein the operations further comprise:
   receive a user input in response to the adjusting the setting of the hearing device or the providing the option to implement the alternative setting, and
   transmit the user input or transmit the provided option to a wireless communication device.

8. A method for operating a hearing device, the method comprising:
   receiving a vital sign for a hearing device user from a sensor of a hearing device worn by the hearing device user;
   determining a classification of sound received by a microphone of the hearing device;
   determining a signal processing scheme to apply to the received sound based on the classification of the received sound;
   providing an output to the hearing device user based on the signal processing scheme;
   determining whether the applied signal processing scheme causes the hearing device user stress based on detecting a change in the vital sign of the hearing device user in response to providing the sound;
   in response to determining the hearing device user is stressed, adjusting a setting of the hearing device or providing an option to implement an alternative setting; and
   logging that the hearing device user is having a negative hearing experience associated with the applied signal processing scheme or the provided alternative setting, wherein logging includes storing the classification of sound received at the hearing device.

9. The method of claim 8, the method further comprising:
   after providing the adjusted setting or providing the option to implement the alternative setting, determining that the hearing device user is still stressed based on a further change of the vital sign of the hearing device user or the vital sign remaining the same and logging that the hearing device user is still having negative hearing experience based on the adjusted setting or the providing the option to implement the alternative option.

10. The method of claim 8, the method further comprising:
    in response to determining that the hearing device user is not stressed, logging information indicating that the hearing device user is having a positive hearing experience associated with the applied signal processing scheme; and
    transmitting the logged information to a wireless communication device.

11. The method of claim 8, wherein determining the applied signal processing scheme to apply to the hearing device is based on a machine learning algorithm that is trained on a dataset of hearing device users receiving the same or similar sound.

12. The method of claim 8, the method further comprises:
    receiving a user input in response to the adjusting the setting of the hearing device or the providing the option to implement the alternative setting, and
    transmitting the user input or transmitting the provided option to a wireless communication device.

13. The method of claim 8, wherein the vital sign is associated with temperature, pulse, heart measurable parameters, sweat, a breathing pattern, a voice of the hearing device user, speech of the hearing device user, or skin conductance of the hearing device user.

14. The method of claim 8, wherein the method further comprises:
    receiving a user input to implement the alternative setting; and
    in response to the received user input, executing an operation to implement the alternative setting.

15. The method of claim 8, wherein the method further comprises:
    receiving additional information regarding the hearing device user; and
    determining, based on the additional information, whether the hearing device user is stressed for a reason not related to the received sound or the applied signal processing scheme.

16. The method of claim 8, wherein the method further comprises:
    providing feedback to the hearing device based on logging at least one of the received sound or the applied signal processing scheme and whether the hearing device user was stressed, wherein the feedback is used in determining the signal processing scheme.

17. A non-transitory computer-readable medium storing instructions that when executed by a processor direct a hearing device to perform operations, the operations comprising:
    receive a vital sign for a hearing device user from a sensor of a hearing device worn by the hearing device user;
    determine a classification of sound received by a microphone of the hearing device;
    determine a signal processing scheme to apply to the received sound based on the classification of the received sound;
    provide an output to the hearing device user based on the signal processing scheme;
    determine whether the applied signal processing scheme causes the hearing device user stress based on detecting a change in the vital sign of the hearing device user in response to providing the sound;
    in response to determining the hearing device user is stressed, adjust a setting of the hearing device or provide an option to implement an alternative setting; and
    after providing the adjusted setting or providing the option to implement the alternative setting, determine that the hearing device user is still stressed based on a further change of the vital sign of the hearing device user or the vital sign remaining the same and log that the hearing device user is still having negative hearing experience based on the adjusted setting or the providing the option to implement the alternative setting.

18. The non-transitory computer readable medium of claim 17, wherein the vital sign is associated with temperature, pulse, heart measurable parameters, sweat, a breathing pattern, a voice of the hearing device user, speech of the hearing device user, or skin conductance of the hearing device user.

* * * * *